United States Patent [19]

Riegel

[11] 3,968,050

[45] July 6, 1976

[54] OXIDATION OF MOLTEN SALTS AND RECOVERY OF CHLORINE VALUES

[75] Inventor: Herbert Riegel, Maplewood, N.J.

[73] Assignee: The Lummus Company, Bloomfield, N.J.

[22] Filed: Mar. 12, 1974

[21] Appl. No.: 450,456

[52] U.S. Cl. ............... 252/187 R; 252/186; 260/654 A; 260/656 R; 260/659 A; 260/662 A; 260/DIG. 42; 423/46; 423/472; 423/493
[51] Int. Cl.$^2$ ............... C01B 9/02; C07C 17/00; C07C 21/06
[58] Field of Search ............... 252/187 R, 182, 186; 260/659 A, 662 A, 654 A, DIG. 42; 423/46, 493, 472

[56] References Cited
UNITED STATES PATENTS

| | | | |
|---|---|---|---|
| 3,548,016 | 12/1970 | Sze | 260/659 R |
| 3,776,967 | 12/1973 | Riegel et al. | 260/659 A |
| 3,869,518 | 3/1975 | Sze et al. | 60/656 R |
| 3,879,481 | 4/1975 | Sze et al. | 260/656 R |

Primary Examiner—Herbert B. Guynn
Attorney, Agent, or Firm—Marn & Jangarathis

[57] ABSTRACT

In the oxidation of a molten salt, such as copper chlorides with the simultaneous recovery of chlorine values, as chlorine and/or hydrogen chloride, oxygen is introduced into a lower bed and chlorine values are introduced into an upper bed for contact with downwardly flowing melt. By reversing the point of introduction of chlorine values and oxygen, the overall bed contact area required is increased.

6 Claims, 1 Drawing Figure

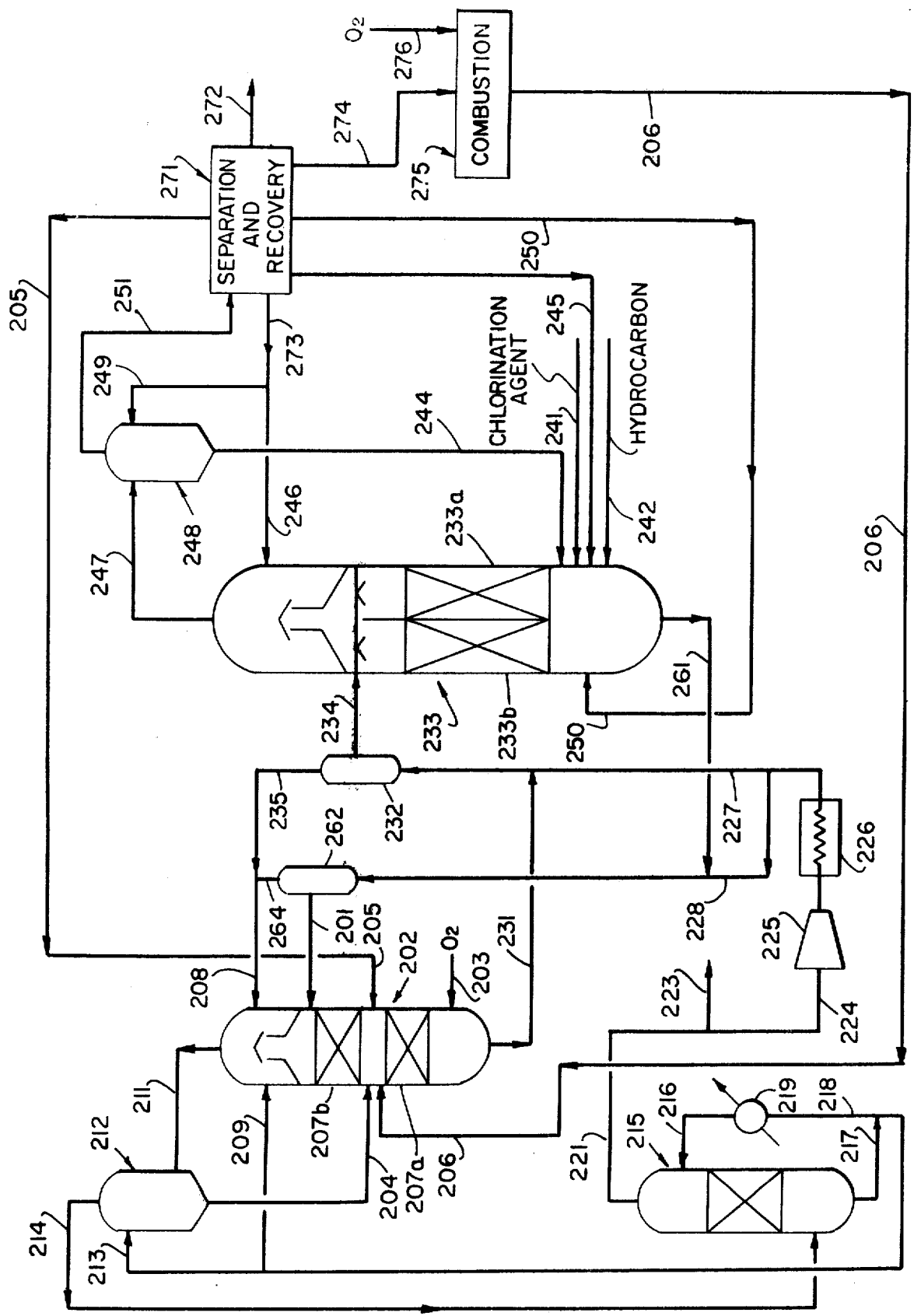

OXIDATION OF MOLTEN SALTS AND RECOVERY OF CHLORINE VALUES

This invention relates to the oxidation of molten salts and simultaneous recovery of chlorine values. This invention further relates to the production of chlorinated hydrocarbons by the use of molten salts.

In U.S. Pat. No. 3,548,016, there is described a process wherein chlorine values are recovered in an oxidation reactor by direct contact with a molten salt and wherein the salt is oxidized by direct contact with molecular oxygen.

Similarly, in U.S. Pat. application Ser. No. 95,030 filed on Dec. 4, 1970, now U.S. Pat. No. 3,879,481 there is described a process for producing vinyl chloride wherein, in the molten salt oxidation zone, a molten salt containing the higher and lower valent chlorides of a multivalent metal is contacted with molecular oxygen to produce the oxychloride of the metal, and wherein the salt is also contacted with a gas containing chlorine and/or hydrogen chloride whereby the chlorine and/or hydrogen chloride is absorbed by the molten salt by generation of additional higher valent metal chloride.

An object of the present invention is to provide an improvement in a process for oxidizing a molten salt.

Another object of the present invention is to provide an improved process for recovering the chlorine values, by use of a molten salt, in conjunction with oxidation of the salt.

A further object of the present invention is to provide an improved molten salt chlorination process, which includes oxidation of molten salts.

These and other objects of the present invention should be more readily apparent from reading the following description of the present invention.

In accordance with the present invention, a molten salt containing a multivalent metal chloride in its higher and lower valence state is introduced into the upper part of an oxidation reaction zone, and molecular oxygen is introduced into the lower portion of the oxidation reaction zone. Chlorine values which are to be recovered by direct contact with the molten salt are introduced into an intermediate portion of the reaction zone; i.e., above the introduction point of molecular oxygen.

In the oxidation zone, the molten salt is countercurrently contacted with the chlorine values and the molecular oxygen, resulting in recovery of the chlorine values by enriching the salt in the higher valent metal chloride, and oxidation of the molten salt to produce the oxychloride of the multivalent metal. In accordance with the present invention, the points of introduction of oxygen and chlorine values, as compared to prior art processes, are reversed, and as a result of such reversal, the overall contact area required for the reaction zone is reduced.

The chlorine values which are recovered in the melt oxidation reaction zone are in the form of either chlorine, hydrogen chloride or mixtures thereof. The chlorine values may be introduced into the oxidation reaction zone in gaseous form or in liquid form, as for example, in the form of aqueous hydrogen chloride, or may be introduced in both gaseous and liquid form. At least a portion of the chlorine values, which are recovered in the oxidation reaction zone, are generally derived from the combustion of by-product chlorinated hydrocarbon, the aforesaid combustion producing an effluent containing chlorine, hydrogen chloride, carbon oxide(s), and water vapor. The direct contact between the molten salt and the combustion effluent results in selective absorption, by the melt, of the chlorine values.

A portion of the chlorine values which are introduced into the oxidation reaction zone may be in the form of aqueous hydrogen chloride. The aqueous hydrogen chloride may be derived from aqueous hydrogen chloride used for quenching the gaseous effluent from the oxidation reaction zone, as hereinafter described. The aqueous hydrogen chloride could also be derived from hydrogen chloride present in an effluent from a chlorination reaction zone.

In accordance with the present invention, the oxidation reaction zone is preferably comprised of a single reactor containing two packed beds, or other means for increasing contact between the melt and the oxygen and the chlorine-values, with the molecular oxygen being introduced into the lowest bed and the chlorine values being introduced into one of the beds above the bed into which the molecular oxygen is introduced. In this manner, the lowest bed of the reactor is used solely for oxidation of the melt, whereas in the upper bed(s) both chlorination (by recovery of chlorine values) and oxidation of the melt is effected.

The melts employed in the present invention include the higher and lower valent forms of a chloride of a multivalent metal; i.e., a metal having more than one positive valence state, such as manganese, iron, copper, cobalt and chromium, preferably copper. In the case of higher melting multivalent metal chlorides, such as copper chlorides, a metal salt melting point depressant, which is non-volatile and resistant to the action of oxygen at the process conditions, such as a chloride of a univalent metal; i.e., a metal having only positive valence state, is added to the multivalent metal chloride to form a molten salt mixture having a reduced melting point. The univalent metal chlorides, are preferably alkali metal chlorides, such as potassium and lithium chlorides in particular, but it is to be understood that other metal chlorides and mixtures thereof, such as the heavy metal chlorides, i.e., heavier than copper, of Groups I, II, III, and IV of the Periodic Table; e.g., zinc, silver and thallium chloride, may also be employed. The metal chloride melting point depressant is added in an amount sufficient to maintain the salt mixture as a melt at the reaction temperatures, and is generally added in an amount sufficient to adjust the melting point of the molten salt mixture to a temperature of below about 500°F. In the case of a salt mixture of copper chlorides and potassium chloride, the composition of the melt ranges between about 20% to about 40%, preferably about 30%, by weight, potassium chloride with the remainder being copper chlorides. It is to be understood, however, that in some cases the catalyst melt may have a melting point higher than 500°F, provided the catalyst remains in the form of the melt throughout the processing steps. It is further to be understood that the melt may contain a mixture of multivalent metal chlorides or other reaction promoters. It is also to be understood that in some cases, metal chloride may be maintained in molten form without a melting point depressant.

The reactions for recovery of chlorine values and oxidation of the molten salt may be represented by the following equations, using copper chloride, as a representative multivalent metal chloride:

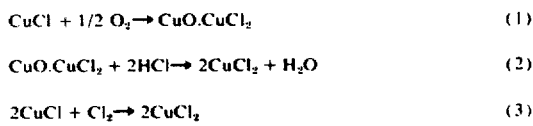

(1) $CuCl + 1/2\ O_2 \rightarrow CuO \cdot CuCl_2$ (2) $CuO \cdot CuCl_2 + 2HCl \rightarrow 2CuCl_2 + H_2O$ (3) $2CuCl + Cl_2 \rightarrow 2CuCl_2$ As should be apparent, the oxygen introduced into the oxidation reactor is sufficient to meet the requirements for recovery of hydrogen chloride (Equation 2), and provide for net production of oxychloride.

The oxidation reactor in which both oxidation of the melt and recovery of chlorine values is effected is generally operated at a temperature from about 600° to about 1,000°F, although higher temperatures may be employed. The preferred temperature is in the order of from about 700° to about 950°F. The oxidation reaction pressure is generally in the order from about 1 to about 20 atmospheres, and the residence time is generally in the order from about 1 to about 60 seconds, although longer, or for that matter shorter reaction times may be employed.

The oxidation reactor is generally operated in a manner such that the salt therefrom includes oxychloride in an amount of at least about 0.5%, by weight. In general, the oxychloride content of the melt is from about 0.5% to about 5.5%, and preferably from about 1% to about 3%, all by weight. It is to be understood that lower oxychloride concentrations could be used; i.e., by increasing salt circulation rates.

The oxidized molten salt may be employed for the chlorination (oxychlorination) of a hydrocarbon or partially chlorinated hydrocarbon, such as for example, an aliphatic hydrocarbon (saturated or olefinically unsaturated) or partially chlorinated derivative thereof, preferably those having one to four carbon atoms, or an aromatic hydrocarbon, which includes unsubstituted aromatic hydrocarbons, such as benzene, or alkyl or alkenyl substituted derivatives. The preferred feeds are methane, ethane and/or ethylene and partially chlorinated $C_1$ and $C_2$ hydrocarbons.

The present process is particularly suitable for the production of chlorinated methanes or vinyl chloride by the use of molten salts wherein the oxidized salt from the oxidation reaction zone is employed in a chlorination (oxychlorination) reaction zone for contacting fresh feed (methane or ethylene and/or ethane), hydrogen chloride and/or chlorine and recycle components, with the molten salt, which is withdrawn from the chlorination (oxychlorination) zone, being introduced into the oxidation reaction zone.

The invention will be further described with respect to the following drawing wherein:

The drawing is a simplified schematic flow diagram of an embodiment of the present invention.

The embodiment illustrated in the drawing is particularly described with respect to the production of vinyl chloride from ethane and/or ethylene, but it is to be understood that the teachings of the present invention are also applicable to the production of other chlorinated hydrocarbons by the use of molten salts.

Referring now to the drawing, a molten chloride salt, such as a mixture of potassium chloride, cupric chloride and cuprous chloride, in line 201, is introduced into the top of an oxidation vessel 202, maintained at a pressure from about 1 to about 20 atm. A compressed oxygen-containing gas, such as air, in line 203, an aqueous solution of hydrogen chloride in lines 204 and 205, obtained as hereinafter described, and a by-product combustion effluent, in line 206, comprising chlorine and/or hydrogen chloride, as well as carbon oxides, water vapor and nitrogen, obtained as hereinafter described, are introduced into reactor 202. The reactor 202 includes two packed sections 207a and 207b for increasing contact between the molten salt and the oxygen containing gas, introduced through line 203, and the chlorine values introduced through lines 204, 205, and 206. In accordance with the present invention, the oxygen containing gas is introduced into the lower portion of reactor 202, the chlorine values are introduced into an intermediate portion of the reactor 202 whereby lower bed 207a is only employed for contact between the oxygen containing gas and the molten salt. It is to be understood that although packed beds are employed in reactor 202, the packed beds could be replaced by other suitable means for increasing contact between the molten salt and introduced chlorine values and molecular oxygen. It is also to be understood that although the embodiment is described with reference to three different streams containing chlorine values, the process may be effected with only single stream, either aqueous or vapor, of chlorine values being introduced into reactor 202. Similarly, the streams of chlorine values can be combined instead of being separately introduced into reactor 202. As a result of the countercurrent contact between the feed introduced through lines 203, 204, 205, and 206, and the descending molten salt mixture, the salt is oxidized to produce copper oxychloride, and the hydrogen chloride and/or chlorine introduced with the combustion effluent and the hydrogen chloride introduced as aqueous hydrogen chloride are absorbed by the molten salt to produce cupric chloride. In addition, the water introduced with the aqueous hydrogen chloride is vaporized. The oxygen is introduced in an amount such that copper oxychloride is present in the molten salt withdrawn from reactor 202.

An effluent gas, including water vapor, nitrogen, carbon oxides and unabsorbed hydrogen chloride rises into the top of vessel 202 wherein the effluent gas is combined with lift gas, as hereinafter described, introduced through line 208. The combined gas is directly contacted in the top of vessel 202 with a spray of aqueous hydrogen chloride quench liquid introduced through line 209 to cool the combined gas and eliminate any vaporized and entrained salts therefrom. The effluent gas is cooled to a temperature at which the molten salt is still in the form of a melt to permit the molten salt to flow back into the reactor 202.

The cooled gaseous stream withdrawn from reactor 202 through line 211 is introduced into quench vessel 212 wherein the gaseous stream is directly contacted with an aqueous hydrogen chloride stream introduced therein through line 213. The quenching in vesel 211 is effected in a manner such that the aqueous hydrogen chloride quench liquid introduced through line 213 is partially vaporized which produces a remaining aqueous hydrogen chloride quench liquid having a higher concentration of hydrogen chloride. The quenching in vessel 212 also functions to separate any remaining entrained salt from the gaseous effluent. In accordance with a preferred embodiment, quenching in vessel 212 is effected in a manner to cool the effluent to a temperature from about 200°F to about 250°F.

The remaining liquid aqueous hydrogen chloride quench liquid, containing any remaining salt, is withdrawn from vessel 212 through line 204 and introduced, as recycle feed, into reactor 202.

The effluent gas, now also containing vaporized quench liquid, withdrawn from vessel 212 through line 214 is introduced into a direct contact quench tower 215, of a type known in the art, wherein the gas is cooled by direct contact with aqueous hydrogen chloride quench liquid introduced through line 216. The quenching in tower 215 is controlled in a manner such that not all of the hydrogen chloride present in the off-gas is condensed therefrom in that such complete recovery would be accompanied by an unacceptable corresponding amount of water condensation; accordingly condensation is preferably effected to provide a condensed aqueous hydrogen chloride solution having a hydrogen chloride concentration from about 8% to about 20%, preferably from about 8% to about 16%, all by weight. In general such a result can be achieved by effecting cooling in tower 215 to a temperature from about 140°F to about 190°F.

An aqueous hydrogen chloride solution is withdrawn from tower 215 through line 217 and a first portion thereof passed through line 218, including a suitable cooler 219, for introduction into the quench tower 215 to meet the cooling requirements therefor. A second portion of the aqueous hydrogen chloride is passed through lines 209 and 213 to meet the quenching requirements of reactor 202 and of vessel 212, respectively.

The gas withdrawn from tower 215 through line 221 is caustic and water-washed to remove remaining hydrogen chloride, and a portion thereof released to the atmosphere through line 223. The remaining portion of the gas in line 224 is compressed in compressor 225 and the temperature thereof regulated in a heater 226 prior to passage through lines 227 and 228 for use as lift gas for transporting molten salt, as hereinafter described The molten salt, now containing copper oxychloride, and enriched in cupric chloride, as a result of recovering chlorine values, is withdrawn from the bottom of vessel 202 through line 231 and lifted by the lift gas in line 227 into a separation vessel 232 positioned adjacent the top of the reaction portion of a chlorination vessel 233. In separator 232, the molten salt is separated from the lift gas, with the molten salt being introduced into the top of the reaction portion of chlorination vessel 233 through line 234, and combined with lift gas used for transporting salt to the oxidation reactor 202 for introduction into the quenching portion of vessel 202 through line 208 to thereby separate any entrained and vaporized salt therefrom.

The reaction vessel 233 is divided into two reaction sections 233a and 233b, with reaction section 233a functioning as a chlorination section and section 233b as a dehydrochlorination section. The molten salt in line 234 is introduced into both sections 233a and 233b.

Fresh feed chlorine and/or hydrogen chloride is introduced into the bottom of section 233a through line 241, fresh feed ethane and/or ethylene, preferably ethane, is introduced through line 242 and a recycle stream comprised of ethyl chloride, ethane, and ethylene is introduced through line 245. A liquid chlorinated hydrocarbon stream, obtained as hereinafter described, is also introduced into section 233a through line 244.

The reaction section 233a is operated at temperatures and pressures to effect chlorination, dehydrogenation and dehychlorination of the fresh feed and recycle by direct countercurrent contact of the feed and recycle with the descending molten salt. The reactor temperature is generally from about 700° to about 1000°F.

Recycle dichloroethane, preferably 1,2-dichloroethane, in line 250, is introduced into reaction section 233b, and is counter-currently contacted with the molten salt to effect dehydrochlorination thereof to vinyl chloride.

The effluents from each of the sections 233a and 233b, each containing equilibrium amounts of hydrogen chloride, are combined in the top portion of reactor 233.

An effluent gas, containing vinyl chloride, ethyl chloride, dichloroethane, other chlorinated hydrocarbons (one or more of the following: dichloroethylenes, trichloroethylene, tetrachloroethylene, trichloroethane, and tetrachloroethane), ethane, ethylene, water vapor and some hydrogen chloride, (the major portion of the hydrogen chloride produced from dichloroethane reacts with the oxychloride of the salt) rises into the top of the vessel 233 wherein the effluent gas is directly contacted with a spray of quench liquid, in particular one or more of the chlorinated hydrocarbons produced in reactor 233, introduced through line 246 to cool the effluent gas and thereby eliminate any vaporized and entrained salts therefrom. The effluent gas is cooled to a temperature at which the salt mixture remains in molten form to permit the molten salt to flow back into the reactor 233.

The effluent gas, now containing vaporized quench liquid, is withdrawn from vessel 233 through line 247 and introduced into a quench vessel 248, wherein the effluent gas is contacted with chlorinated hydrocarbon quench liquid in line 249 to further cool the gas and separate any remaining entrained salts. The gas is cooled to a temperature at which essentially no aqueous hydrogen chloride is condensed therefrom. Any chlorinated hydrocarbon condensed in vessel 248 is recycled to reactor 233 through line 244. The effluent gas is withdrawn from vessel 248 through line 251 and treated as hereinafter described.

A molten salt is withdrawn from the bottom of reactor 233, through line 261, and lifted by lift gas in line 228 into a separation vessel 262 positioned adjacent the top of reactor 202. In separator 262, the molten salt is separated from the lift gas, and introduced through line 201 into vessel 202. The lift gas is withdrawn from separator 262 through line 264, and combined with the lift gas in line 235 for introduction into the top quenching section of vessel 202 through line 208.

The reactor effluent in line 251 is introduced into a separation and recovery zone, schematically indicated as 271, to recover various components, with net product; i.e. vinyl chloride, being recovered through line 272. Recycle ethane, ethylene, and ethyl chloride are recovered in zone 271 for introduction into reaction section 233a through line 245. 1,2-dichloroethane is recovered in zone 271 for introduction into reaction section 233b through line 250. An aqueous hydrogen chloride solution may also be recovered, in zone 271, and recycled to reactor 202 through line 205, as described in U.S. Pat application Ser. No. 238,196, filed Mar. 27, 1972, which is hereby incorporated by reference. Chlorinated hydrocarbon quench liquid is also recovered in zone 271, through line 273 for meeting the quench requirements of reactor 233. Similarly, chlorinated hydrocarbon by-products, which are not readily convertible to vinyl chloride, comprised of one or more of the following: dichloroethylenes, trichloroethylene, tetrachloroethylene, trichloroethanes, and tetrachloroethanes, are recovered in zone 271 through line 274. The overall operation of the separation and recovery zone for recovering various components of the effluent is described in more detail in U.S. Pat. application Ser. No. 153,374, filed on June 15, 1971, now U.S. Pat. No. 3,937,744, which is hereby incorporated by reference.

The chlorinated hydrocarbons in line 274 are introduced into a combustion chamber 275, along with an oxygen containing gas such as air, in line 276, to burn the chlorinated hydrocarbons and liberate the chlorine values therefrom. A combustion effluent, containing hydrogen chloride, chlorine, carbon oxides, water vapor and nitrogen is withdrawn from combustion chamber 275 for introduction into reactor 202 through line 206. The details of such recovery of chlorine values are described in U.S. Pat. application Ser. No. 95,030, filed Dec. 4, 1970, now U.S. Pat. No. 3,879,481, which is hereby incorporated by reference.

Although the present invention has been particularly described with respect to the production of vinyl chloride in a system employing two reaction zones in a single reactor, the teachings of the invention are equally applicable to the other embodiments for producing vinyl chloride, described in U.S. Pat. application Ser. No. 153,374 which is referred to above. Thus, for example, as described in U.S. Pat. application Ser. No. 153,374, the chlorination and dehydrochlorination could be effected in a single zone. Similarly, separate reactors could be used for effecting the dehydrochlorination and chlorination reactions.

It is also to be understood that the present invention is also applicable to the chlorination of hydrocarbons other than ethane and/or ethylene. Thus, for example, the hereinabove described embodiment is also particularly suitable for the chlorination of methane, with reactor 233 being comprised of a single reaction section for chlorination of fresh methane feed.

In such an embodiment, methane is introduced into reactor 233 through line 242. The net product recovered in line 272 is generally either carbon tetrachloride or combinations of methyl chloride, methylene chloride, chloroform and carbon tetrachloride. The recycle stream in line 245 contains one or more of methyl chloride, methylene chloride, chloroform and carbon tetrachloride. In the production of chlorinated methanes, the feed to the combustion chamber 275 is generally comprised of dimers of chlorinated methanes. Details of a process for producing chlorinated methanes are described in U.S. Pat. applications Ser. Nos. 299,114, filed Oct. 19, 1972, and 299,848, filed Oct. 24, 1972, which are hereby incorporated by reference.

The invention will be further described with respect to the following example but the scope of the invention is not to be limited thereby.

EXAMPLE

A molten salt mixture as reported in Table I, is oxidized in reactor 202 while simultaneously recovering chlorine values, and is than employed for producing vinyl chloride from ethane.

Molecular oxygen is introduced through line 203 at the rate of 40,736 lbs/hr; and hydrogen chloride, as an aqueous solution, is introduced through lines 204 and 205 at the rate of 4015 lbs/hr and 1733 lbs/hr respectively. The combustion effluent introduced through line 206 included 18,200 lbs/hr of chlorine values as hydrogen chloride and chlorine.

Reactor 202 is operated at an average salt temperature of 860°F and a pressure of 50 psig.

The molten salt is used in reactor 233, operated at a pressure of 50 psig and an average salt temperature of 860°F to produce, as net product, in line 272, 62,500 lbs/hr of vinyl chloride.

The net feed to reactor 233 is 33,180 lbs/hr of ethane and 35,750 lbs/hr of chlorine.

Table I

|         | Line 201 MM lb/Hr. | Line 234 MM lb/Hr. |
|---------|--------------------|--------------------|
| KCl     | 5.765              | 5.765              |
| CuCl    | 9.690              | 9.206              |
| $CuCl_2$| 4.880              | 5.243              |
| CuO     | —                  | 0.174              |

The present invention is particularly advantageous in that by effecting molten salt oxidation and chlorine value recovery, with the oxygen being introduced into the oxidation reactor at a point below the point of introduction of chlorine values, as compared to the prior art, wherein oxygen is introduced at a point above the point of introduction of chlorine values, there is a significant reduction in the overall required contact area for the oxidation reactor. Thus, for example, by reversing the points of introduction of chlorine values and oxygen in accordance with the invention, overall oxidation reactor bed transfer area can be reduced by as much as about 45%.

Numerous modifications and variations of the present invention are possible in light of the above teachings and, therefore, within the scope of the appended claims the invention may be practised otherwise than as particularly described.

What is claimed:

1. In the process for oxidizing a molten salt and recovering chlorine values wherein a molten salt mixture containing a multivalent metal chloride in its higher and lower valence state is contacted in a reaction zone with chlorine values selected for the group consisting of chlorine, hydrogen chloride and mixtures thereof to recover the chlorine values by generation of the higher valent chloride and is also contacted with molecular oxygen to produce the oxychloride of the multivalent metal, said multivalent metal chloride being selected from the group consisting of the chlorides of copper, chromium, manganese, iron and cobalt, said reaction zone being operated at a temperature from about 600° to about 1000°F, the improvement comprising:

introducing the molten mixture into an upper portion of said reaction zone;

introducing the chlorine values into an intermediate portion of said reaction zone;

introducing molecular oxygen into a lower portion of said reaction zone, passing the molten mixture through said reaction zone in countercurrent contact with said chlorine values and molecular oxygen to recover the chlorine values and produce oxychloride; and recovering molten salt from said reaction zone having an increased content of the higher valent metal chloride and containing the oxychloride of the multivalent metal.

2. The process of claim 1 wherein the reaction zone contains first and second packed beds, said first packed bed being positioned below the second packed bed, the molecular oxygen being introduced into the first bed and the chlorine values into the second packed bed, whereby the first packed bed is employed solely for oxidation of the melt.

3. The process of claim 2 wherein the multivalent metal chloride is copper chloride.

4. The process of claim 3 wherein at least a portion of the chlorine values are introduced into the reaction zone as aqueous hydrogen chloride.

5. The process of claim 3 wherein at least a portion of the chlorine values are introduced into the reaction zone as a gaseous stream comprising chlorine and hydrogen chloride.

6. The process of claim 3 wherein the chlorine values are introduced into the reaction zone as aqueous hydrogen chloride and a gas stream comprising chlorine and hydrogen chloride.

* * * * *